US00PP21584P2

(12) United States Plant Patent
Endisch

(10) Patent No.: US PP21,584 P2
(45) Date of Patent: Dec. 21, 2010

(54) ***MANDEVILLA* PLANT NAMED 'GENDIPSA'**

(50) Latin Name: *Mandevilla×amabilis*
Varietal Denomination: Gendipsa

(75) Inventor: Gerd Endisch, Hagenbach (DE)

(73) Assignee: Willi Endisch Gbr, Hagenbach (DE)

( * ) Notice: Subject to any disclaimer, the term of this patent is extended or adjusted under 35 U.S.C. 154(b) by 0 days.

(21) Appl. No.: 12/454,437

(22) Filed: May 18, 2009

(51) Int. Cl.
*A01H 5/00* (2006.01)

(52) U.S. Cl. ..... Plt./232

(58) Field of Classification Search ..... Plt./232
See application file for complete search history.

(56) References Cited

PUBLICATIONS

Upov-rom GTITM Plant Variety Database 2009/06, GTI Jouve Retrieval Software, Citation for *Mandevilla* 'Gendipsa', one page.*

* cited by examiner

*Primary Examiner*—June Hwu
(74) *Attorney, Agent, or Firm*—Mark P. Bourgeois

(57) ABSTRACT

A new and distinct cultivar of *Mandevilla* plant named 'Gendipsa' that is characterized by double red purple flowers, medium green elliptical shaped leaves and a compact growth habit.

1 Drawing Sheet

Botanical classification: *Mandevilla×amabilis.*
Variety denomination: 'Gendipsa'.

BACKGROUND OF THE INVENTION

The present invention relates to a new and distinct cultivar of *Mandevilla* plant botanically known as *Mandevilla×amabilis* and hereinafter referred to by the cultivar name 'Gendipsa'.

The new cultivar is the product of a breeding program conducted by the inventor in a cultivated area of Hagenbach, Germany. The objective of the breeding program is to develop new *Mandevilla* cultivars that have double flowers and a compact habit.

'Gendipsa' originated from the hybridization of the female or seed parent a proprietary selection of *Mandevilla×amabilis* identified as 'DP 524' (not patented) and the male or pollen parent a proprietary selection of *Mandevilla×amabilis* identified as 'DP 100' (not patented). The cultivar 'Gendipsa' was selected by the inventor in June of 2005 as a single plant within the progeny of the stated cross in a controlled environment of Hagenbach, Germany.

Asexual reproduction by terminal cuttings of the new cultivar 'Gendipsa' were first done in September of 2006 in Hagenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Mandevilla* cultivar 'Gendipsa'. These traits in combination distinguish 'Gendipsa' as a new and distinct cultivar apart from other known existing varieties of *Mandevilla.*

1. *Mandevilla* 'Gendipsa' exhibits double red purple flowers.
2. *Mandevilla* 'Gendipsa' exhibits medium green elliptical shaped leaves.
3. *Mandevilla* 'Gendipsa' exhibits a compact growth habit.

The closest comparison variety is *Mandevilla* 'Monite' (U.S. Plant Pat. No. 12,123). 'Gendipsa' is different than 'Monite' in having flowers that are larger and more purple, shorter petioles and darker green leaves.

The new cultivar 'Gendipsa' is distinguishable from the female parent *Mandevilla* 'DP 524' in having darker green leaves, a more compact habit and darker red purple double flowers. The flowers of 'DP 524' are semi-double.

The new cultivar 'Gendipsa' is distinguishable from the male parent *Mandevilla* 'DP 100' in having a more compact habit and lighter red purple double flowers. The flowers of 'DP 100' are single.

BRIEF DESCRIPTION OF THE DRAWING

The accompanying photograph illustrates the distinguishing traits of *Mandevilla* 'Gendipsa'. The plant in the photograph shows an overall view of a 8 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Mandevilla* cultivar named 'Gendipsa'. Data was collected in Hagenbach, Germany from 8 month old plants grown under glass greenhouse conditions. The plants were grown in 25 cm. diameter containers. The time of year was Spring and the daytime temperature ranged from 18 to 26° Centigrade. The temperature at night ranged from 16 to 20° Centigrade. The light level was 20 to 35 klux. No photoperiodic treatments were used. Growth retardant was applied at a rate of 0.05 percent. Color determinations are in accordance with The Royal Horticultural Society Colour Chart 2001 edition, except where general color terms of ordinary dictionary significance are used. The growing requirements are similar to the species.

'Gendipsa' has not been tested under all possible conditions and phenotypic differences may be observed with variations in environmental, climatic, and cultural conditions, however, without any variance in genotype.

Botanical classification: *Mandevilla×amabilis* cultivar 'Gendipsa'.

Parentage: 'Gendipsa' resulted from the hybridization of the following parent plants.

*Female parent.*—A proprietary selection of *Mandevilla×amabilis* identified as 'DP 524'.

*Male parent.*—A proprietary selection of *Mandevilla×amabilis* identified as 'DP 100'.

Vigor: Moderate.

Propagation: Terminal cuttings.

Time to initiate roots: Approximately 21 days to produce roots on an initial cutting.

Time to produce a rooted cutting or liner: Approximately 35 days.

High temperature tolerance: 40 degrees Centigrade.

Low temperature tolerance: 0 degrees Centigrade.

Root system: Fine and fibrous.

Growth habit: Upright and vining plant habit.

Plant height including twines: 160 cm.

Lateral branch: Length: About 120 cm. Diameter: About 3.0 mm.

Internode length: About 12.0 cm.

Strength: Strong.

Texture: Smooth, glabrous.

Color: 146 D.

Foliage:

*Arrangement.*—Opposite, simple.

*Length.*—Fully expanded leaves: About 14 cm. Width. — About 6,0 cm.

*Shape.*—Elliptic.

*Apex.*—Cuspidate.

*Base.*—Rounded to cordate.

*Margin.*—Entire.

*Texture, upper and lower surfaces.*—Smooth, glabrous.

*Venation pattern.*—Pinnate, reticulate.

*Color.*—Developing foliage, upper surface: 137B. Developing foliage, lower surface: 146C to 146D. Fully expanded foliage, upper surface: 135A; venation, 145D. Fully expanded foliage, lower surface: 147B to 147C; venation, 145D.

*Petiole length.*—About 0.5 cm.

*Petiole diameter.*—About 4.0 mm.

*Petiole texture upper and lower surfaces.*—Smooth, glabrous.

*Petiole color upper and lower surfaces.*—145D.

Flower:

*Flower type and habit.*—Double flowers; flowers racemose; flowers face mostly outwardly; Flowers not persistent; Freely flowering habit, about five flowers per inflorescence; about 3 open flowers per inflorescence, 5 to 9 inflorescences per plant.

*Natural flowering season.*—Long flowering period; summer to late autumn; flowering continuous during this period.

*Flower longevity on the plant.*—About 3 to 6 weeks.

*Fragrance.*—None detected.

*Inflorescence length.*—Without peduncle: About 18 cm. including peduncle: 34 cm.

*Inflorescence diameter.*—About 16 cm.

*Flowers.*—Appearance: Flared trumpet, corolla fused, five-parted; petals imbricate; flowers roughly star-shaped.

*Diameter.*—10 to 11.5 cm. Depth (length): About 7.5 cm.

*Flower buds.*—Length: 2.5 to 6.0 cm. Diameter: 1.5 to 4.0 cm. Shape: Oblong. Color: 62C.

*Corolla.*—Arrangement/appearance: Two whorls of five petals, fused into flared trumpet; petals imbricate.

*Petal length.*—About 6.5 cm. Petal width: About 4.2 cm.

*Petal shape.*—Spatulate.

*Petal apex.*—Acuminate.

*Petal margin.*—Entire, undulate.

*Petal texture, upper and lower surfaces.*—Smooth, glabrous.

*Color.*—Petal, when opening, upper surface: between 54 A and B. Petal, when opening, lower surface: between 54 A and B. Petal, fully opened, upper surface: between 54 A and B; Petal, fully opened, lower surface: between 54 A and B; Outer flower tube 54B, Inner throat 54C, Inner throat base 10B.

Sepals:

*Arrangement/appearance.*—Five per flower in a single whorl; fused.

*Length.*—About 5.5 mm. Width: About 1.5 mm.

*Shape.*—Lanceolate.

*Apex.*—Aristate.

*Margin.*—Entire.

*Texture, upper and lower surfaces.*—Smooth, glabrous.

*Color, upper surface.*—144A. Color, lower surface: 144B. Color of the top: 53B.

Peduncles:

*Length.*—12 to 16 cm. Diameter: About 2.5 mm.

*Texture.*—Smooth, glabrous.

*Strength.*—Flexible, but strong.

*Color.*—144A.

Pedicels:

*Length.*—About 1.3 cm. Diameter: About 2.1 mm.

*Texture.*—Smooth, glabrous.

*Strength.*—Flexible, but strong.

*Color.*—182 A.

Seed: Seed production has not been observed.

Disease and pest resistance: Plants of the new *Mandevilla* have not been observed for disease or pest resistance.

The invention claimed is:

1. A new and distinct variety of *Mandevilla* plant named 'Gendipsa' as described and illustrated.

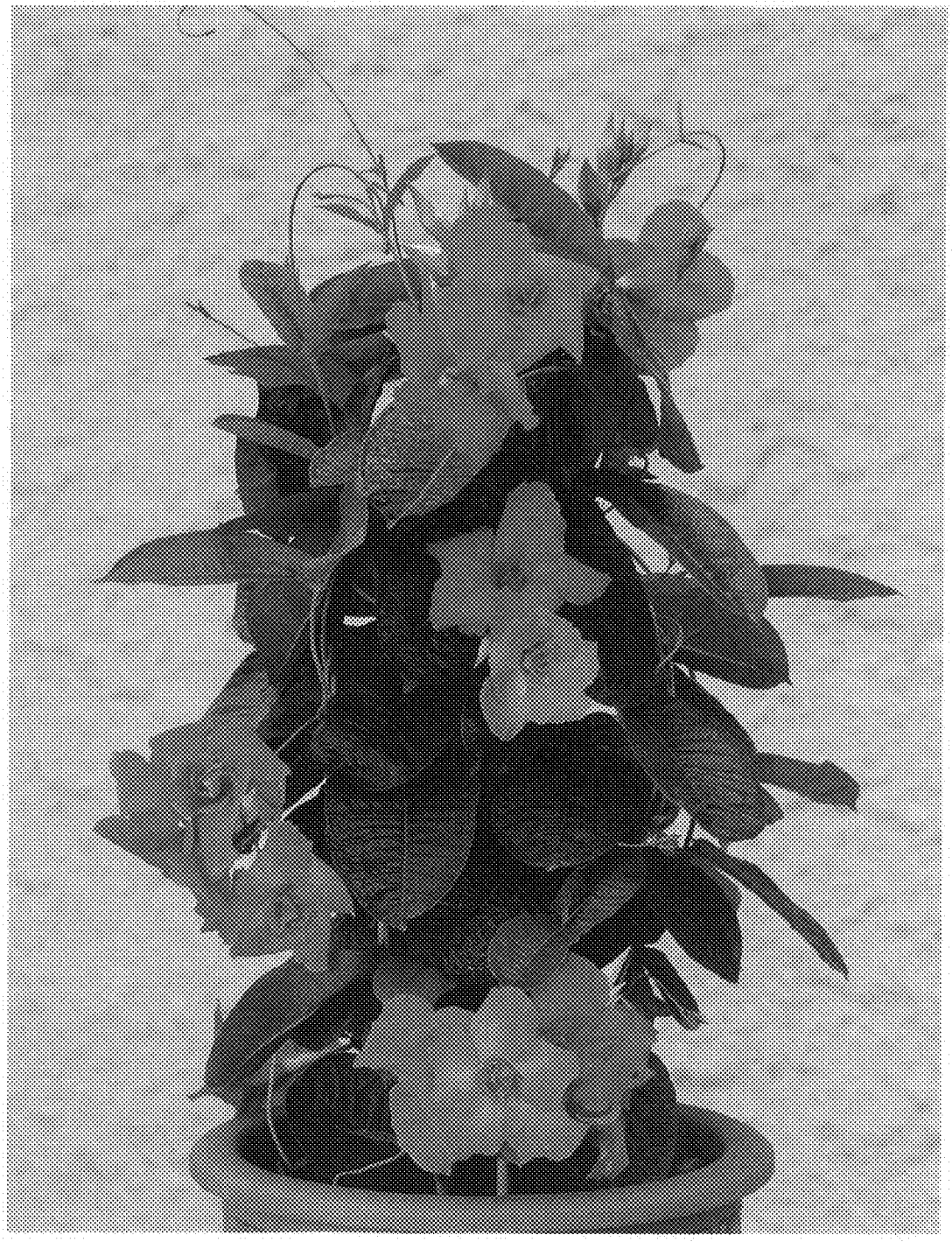

* * * * *